US009504776B2

(12) United States Patent
Farnan et al.

(10) Patent No.: US 9,504,776 B2
(45) Date of Patent: *Nov. 29, 2016

(54) CANNULA LINED WITH TISSUE IN-GROWTH MATERIAL AND METHOD OF USING THE SAME

(75) Inventors: Robert C. Farnan, Rivervale, NJ (US); Oliver Marseille, Aachen (DE)

(73) Assignee: CircuLite, Inc., Teaneck, NJ (US)

( * ) Notice: Subject to any disclaimer, the term of this patent is extended or adjusted under 35 U.S.C. 154(b) by 1265 days.

This patent is subject to a terminal disclaimer.

(21) Appl. No.: 13/025,845

(22) Filed: Feb. 11, 2011

(65) Prior Publication Data

US 2011/0196191 A1   Aug. 11, 2011

Related U.S. Application Data

(60) Provisional application No. 61/303,351, filed on Feb. 11, 2010.

(51) Int. Cl.
| | | |
|---|---|---|
| *A61N 1/362* | (2006.01) | |
| *A61M 1/12* | (2006.01) | |
| *A61M 1/36* | (2006.01) | |
| *A61M 1/10* | (2006.01) | |
| *A61B 17/00* | (2006.01) | |

(52) U.S. Cl.
CPC ............ *A61M 1/122* (2014.02); *A61M 1/1008* (2014.02); *A61M 1/3653* (2013.01); *A61M 1/3659* (2014.02); *A61B 2017/00252* (2013.01); *A61F 2210/0076* (2013.01)

(58) Field of Classification Search
CPC ............ A61B 2017/00252; A61F 2210/0076; A61M 1/1008; A61M 1/122; A61M 1/3653; A61M 1/3659

USPC ........................................................ 607/116
See application file for complete search history.

(56) References Cited

U.S. PATENT DOCUMENTS

| | | | |
|---|---|---|---|
| 3,843,974 | A | 10/1974 | Miller et al. |
| 3,903,895 | A | 9/1975 | Alley et al. |
| 4,033,331 | A | 7/1977 | Guss et al. |

(Continued)

FOREIGN PATENT DOCUMENTS

| | | |
|---|---|---|
| EP | 0241838 A2 | 10/1987 |
| EP | 1839601 A1 | 10/2007 |

(Continued)

OTHER PUBLICATIONS

U.S. Patent and Trademark Office, International Search Report and Written Opinion in corresponding PCT Application No. PCT/US11/46772 mailed Dec. 8, 2011, 7 pp.

(Continued)

*Primary Examiner* — William Levicky
*Assistant Examiner* — Lindsey G Hankins
(74) *Attorney, Agent, or Firm* — Wood Herron & Evans LLP

(57) ABSTRACT

A cannula for moving fluids between a pump and the circulatory system of a patient. The cannula includes a liner having an intermediate portion between a proximal portion and a distal portion, and a lumen extending between the proximal and distal portions. At least the intermediate portion of the liner is constructed from a tissue in-growth material for supporting the growth of endothelial cells. A jacket surrounds at least part of the liner.

52 Claims, 11 Drawing Sheets

(56) References Cited

U.S. PATENT DOCUMENTS

| | | | |
|---|---|---|---|
| 4,790,825 A | 12/1988 | Bernstein et al. | |
| 5,190,528 A | 3/1993 | Fonger et al. | |
| 5,443,497 A | 8/1995 | Venbrux | |
| 5,456,712 A | 10/1995 | Maginot | |
| 5,676,670 A | 10/1997 | Kim | |
| 5,704,372 A * | 1/1998 | Moll et al. | 128/898 |
| 5,738,649 A | 4/1998 | Macoviak | |
| 5,797,960 A | 8/1998 | Stevens et al. | |
| 5,858,009 A | 1/1999 | Jonkman | |
| 5,944,745 A | 8/1999 | Rueter | |
| 5,947,940 A | 9/1999 | Beisel | |
| 5,961,545 A | 10/1999 | Lentz et al. | |
| 5,965,089 A | 10/1999 | Jarvik et al. | |
| 6,019,788 A | 2/2000 | Butters et al. | |
| 6,176,848 B1 | 1/2001 | Rau et al. | |
| 6,186,999 B1 | 2/2001 | Chen | |
| 6,217,546 B1 | 4/2001 | Hinchliffe et al. | |
| 6,299,575 B1 * | 10/2001 | Bolling | 600/16 |
| 6,358,532 B2 | 3/2002 | Starling et al. | |
| 6,475,232 B1 | 11/2002 | Babbs et al. | |
| 6,524,334 B1 | 2/2003 | Thompson | |
| 6,558,414 B2 | 5/2003 | Layne | |
| 6,565,536 B1 | 5/2003 | Sohn | |
| 6,579,314 B1 | 6/2003 | Lombardi et al. | |
| 6,652,544 B2 | 11/2003 | Houser et al. | |
| 6,740,115 B2 | 5/2004 | Lombardi et al. | |
| 6,770,087 B2 | 8/2004 | Layne et al. | |
| 6,786,920 B2 | 9/2004 | Shannon et al. | |
| 6,790,225 B1 | 9/2004 | Shannon et al. | |
| 6,808,533 B1 | 10/2004 | Goodwin et al. | |
| 6,866,805 B2 | 3/2005 | Hong et al. | |
| 6,911,040 B2 | 6/2005 | Johnson et al. | |
| 6,926,662 B1 | 8/2005 | Aboul-Hosn et al. | |
| 6,946,173 B2 | 9/2005 | Lim et al. | |
| 6,955,175 B2 | 10/2005 | Stevens et al. | |
| 6,984,243 B2 | 1/2006 | Dwyer et al. | |
| 6,989,071 B2 | 1/2006 | Kocur et al. | |
| 6,994,666 B2 | 2/2006 | Shannon et al. | |
| 7,077,801 B2 | 7/2006 | Haverich | |
| 7,083,640 B2 | 8/2006 | Lombardi et al. | |
| 7,108,717 B2 | 9/2006 | Freidberg | |
| 7,699,864 B2 | 4/2010 | Kick et al. | |
| 7,713,193 B2 | 5/2010 | Nance et al. | |
| 7,722,568 B2 | 5/2010 | Lenker et al. | |
| 7,780,692 B2 | 8/2010 | Nance et al. | |
| 2002/0169495 A1 | 11/2002 | Gifford et al. | |
| 2003/0125790 A1 | 7/2003 | Fastovsky et al. | |
| 2003/0149471 A1 | 8/2003 | Briana et al. | |
| 2003/0195535 A1 | 10/2003 | Swanson et al. | |
| 2004/0015150 A1 | 1/2004 | Zadno-Azizi | |
| 2004/0182511 A1 | 9/2004 | Rakos et al. | |
| 2005/0065594 A1 | 3/2005 | DiMatteo et al. | |
| 2005/0124937 A1 | 6/2005 | Kick et al. | |
| 2005/0159711 A1 | 7/2005 | Kathrani et al. | |
| 2005/0183954 A1 * | 8/2005 | Hitchcock et al. | 204/403.01 |
| 2005/0251187 A1 | 11/2005 | Beane et al. | |
| 2006/0052750 A1 | 3/2006 | Lenker et al. | |
| 2006/0064159 A1 | 3/2006 | Porter et al. | |
| 2006/0094983 A1 | 5/2006 | Burbank et al. | |
| 2006/0100565 A1 | 5/2006 | Aboul-Hosn | |
| 2006/0135946 A1 | 6/2006 | Moehle et al. | |
| 2006/0135962 A1 | 6/2006 | Kick et al. | |
| 2006/0135963 A1 | 6/2006 | Kick et al. | |
| 2006/0135981 A1 | 6/2006 | Lenker et al. | |
| 2006/0184088 A1 | 8/2006 | Van Bibber et al. | |
| 2006/0200189 A1 | 9/2006 | Nance et al. | |
| 2006/0235357 A1 | 10/2006 | Woodward et al. | |
| 2006/0253102 A1 | 11/2006 | Nance et al. | |
| 2007/0016165 A1 | 1/2007 | Von Oepen et al. | |
| 2007/0088323 A1 * | 4/2007 | Campbell et al. | 604/523 |
| 2007/0197855 A1 * | 8/2007 | Richardson | A61M 1/3653 600/16 |
| 2007/0197856 A1 | 8/2007 | Gellman et al. | |
| 2008/0109058 A1 | 5/2008 | Greenberg et al. | |
| 2008/0200943 A1 | 8/2008 | Barker et al. | |
| 2008/0215008 A1 | 9/2008 | Nance et al. | |
| 2008/0243081 A1 | 10/2008 | Nance et al. | |
| 2008/0245374 A1 * | 10/2008 | Agnew | 128/887 |
| 2009/0023975 A1 | 1/2009 | Marseille et al. | |
| 2009/0093873 A1 | 4/2009 | Navia | |
| 2009/0112049 A1 | 4/2009 | Ahmed | |
| 2009/0112050 A1 * | 4/2009 | Farnan et al. | 600/16 |
| 2009/0254166 A1 | 10/2009 | Chou et al. | |
| 2009/0287182 A1 | 11/2009 | Bishop et al. | |
| 2009/0287183 A1 | 11/2009 | Bishop et al. | |
| 2010/0016928 A1 * | 1/2010 | Zdeblick et al. | 607/72 |
| 2010/0145267 A1 | 6/2010 | Bishop et al. | |
| 2010/0228077 A1 | 9/2010 | Lenker et al. | |
| 2010/0249491 A1 | 9/2010 | Farnan et al. | |
| 2011/0190567 A1 | 8/2011 | Farnan et al. | |

FOREIGN PATENT DOCUMENTS

| | | |
|---|---|---|
| JP | S6096260 | 5/1985 |
| JP | 6346169 | 2/1988 |
| JP | 4505720 | 10/1992 |
| JP | 09024580 | 1/1997 |
| JP | 09239021 | 9/1997 |
| JP | 2006520621 A | 9/2006 |
| JP | 2008279188 A | 11/2008 |
| JP | 2010104428 A | 5/2010 |
| WO | 9014054 A1 | 11/1990 |
| WO | 99/59652 | 11/1999 |
| WO | 2004082742 A1 | 9/2004 |
| WO | 2005/037345 A2 | 4/2005 |
| WO | 2005037345 A2 | 4/2005 |
| WO | 2010050114 A1 | 5/2010 |

OTHER PUBLICATIONS

U.S. Patent and Trademark Office, International Preliminary Report on Patentability in PCT Application Serial No. PCT/US11/46772, Jul. 29, 2013.

U.S. Patent and Trademark Office, Office Action in U.S. Appl. No. 13/204,201, Mar. 1, 2013.

Japanese Patent Office, Office Action in JP Application No. 2012553039, May 19, 2014.

U.S. Patent and Trademark Office, International Preliminary Report on Patentability in PCT Application No. PCT/US11/24558, Nov. 6, 2012.

U.S. Patent and Trademark Office, Final Office Action in U.S. Appl. No. 13/204,201, Nov. 21, 2012.

United States Patent and Trademark Office, "Non-final Office Action," in related U.S. Appl. No. 13/204,201 mailed on May 9, 2012, 11 pp.

U.S. Patent and Trademark Office, International Preliminary Report on Patentability in corresponding PCT Application No. PCT/US11/24558, Jul. 1, 2012.

U.S. Patent and Trademark Office, International Preliminary Report on Patentability in corresponding PCT Application No. PCT/US11/24533, mailed May 16, 2012, 12 pp.

Douglas B. Cines et al, Endothelial Cells in Physiology and in the Pathophysiology of Vascular Disorders, Blood, 1998, 91:3527-3561.

U.S. Patent and Trademark Office, International Search Report and Written Opinion in PCT Serial No. PCT/US2011/024558, Jul. 1, 2011.

U.S. Patent and Trademark Office, International Search Report and Written Opinion in PCT Serial No. PCT/US2011/024533, Apr. 18 2011.

Japanese Patent Office, Decision of Rejection in JP Application No. 2012553039, Dec. 15, 2014.

European Patent Office, Supplementary European Search Report in EP Application No. 11870615, Nov. 19, 2014.

Alexander Hofmann et al., The effect of human osteoblasts on proliferation and neo-vessel formation of human umbilical vein endothelial cells in a long-term 3A co-culture on polyurethan scaffolds, Article, Biomaterials 29 (2008) 4217-4226.

(56) References Cited

OTHER PUBLICATIONS

Japanese Patent Office, Notice of Reasons for Rejection in JP Application No. 2014-523895, Apr. 20, 2015.
U.S. Patent and Trademark Office, Final Office Action in U.S. Appl. No. 13/204,201, Mar. 13, 2015.
Canadian Patent Office, Office Action in CA Application No. 2787632, Mar. 16, 2015.
Japanese Patent Office, Notice of Reasons for Rejection in JP Application No. 2012-553039, Feb. 8, 2016.
Canadian Intellectual Property Office, Office Action in Canadian Application No. 2787632, Dec. 10, 2015.

* cited by examiner

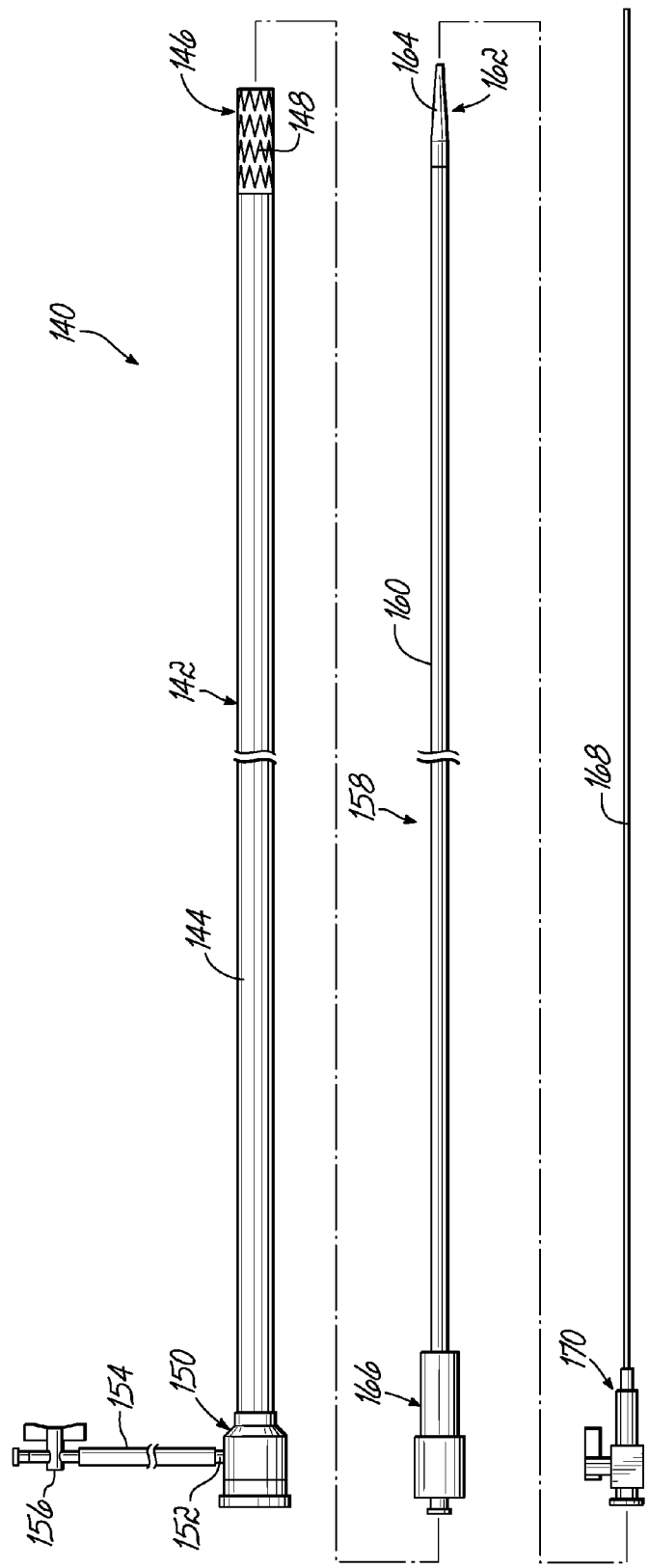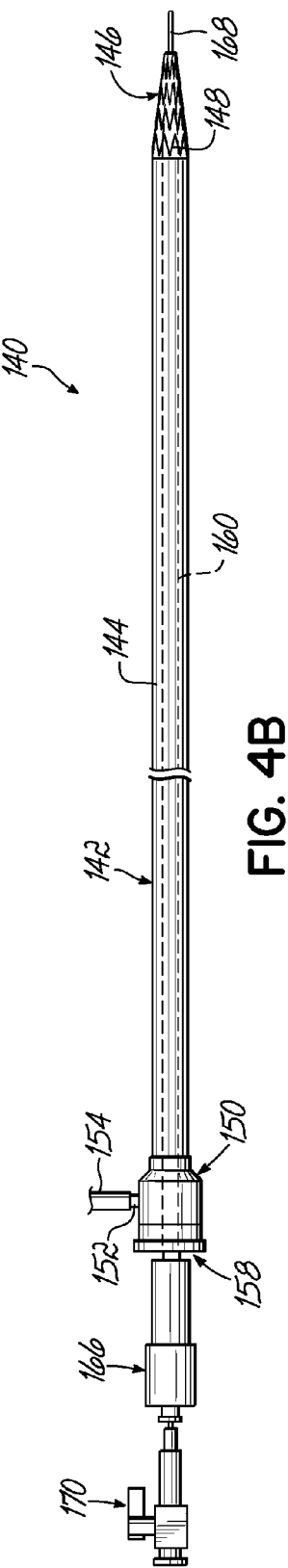
FIG. 4A
FIG. 4B

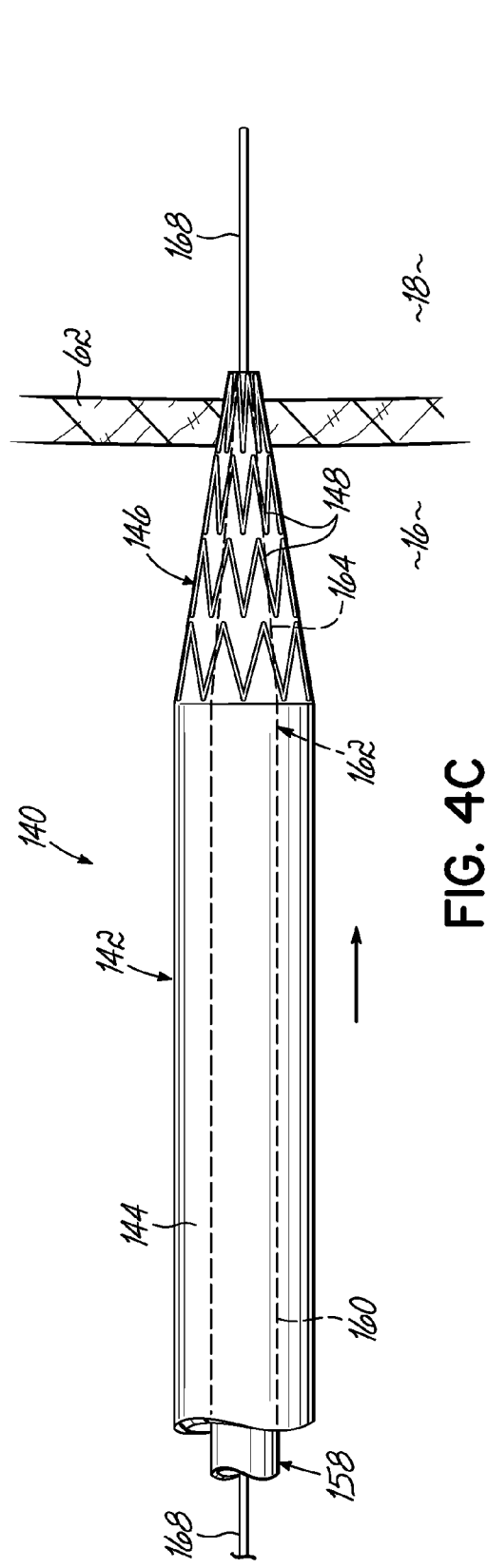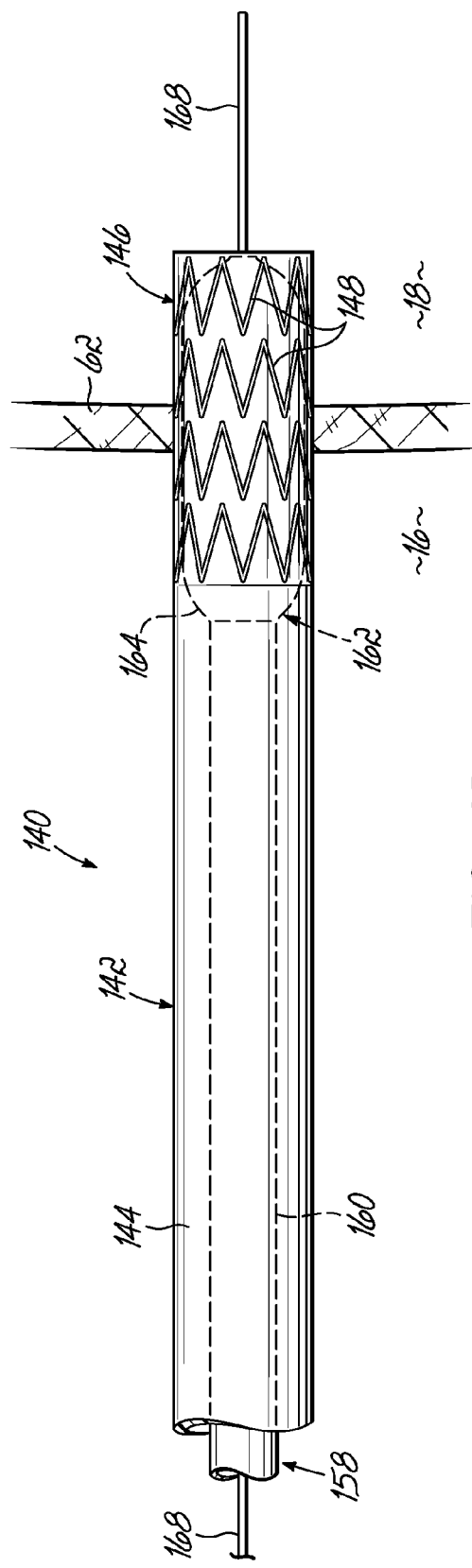
FIG. 4C
FIG. 4D

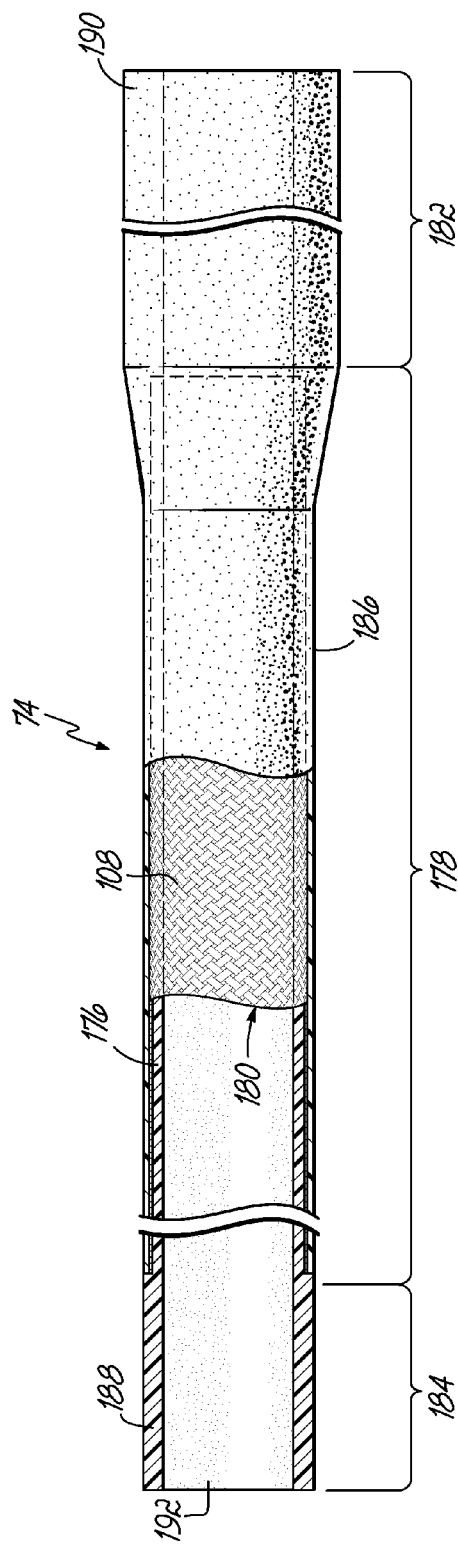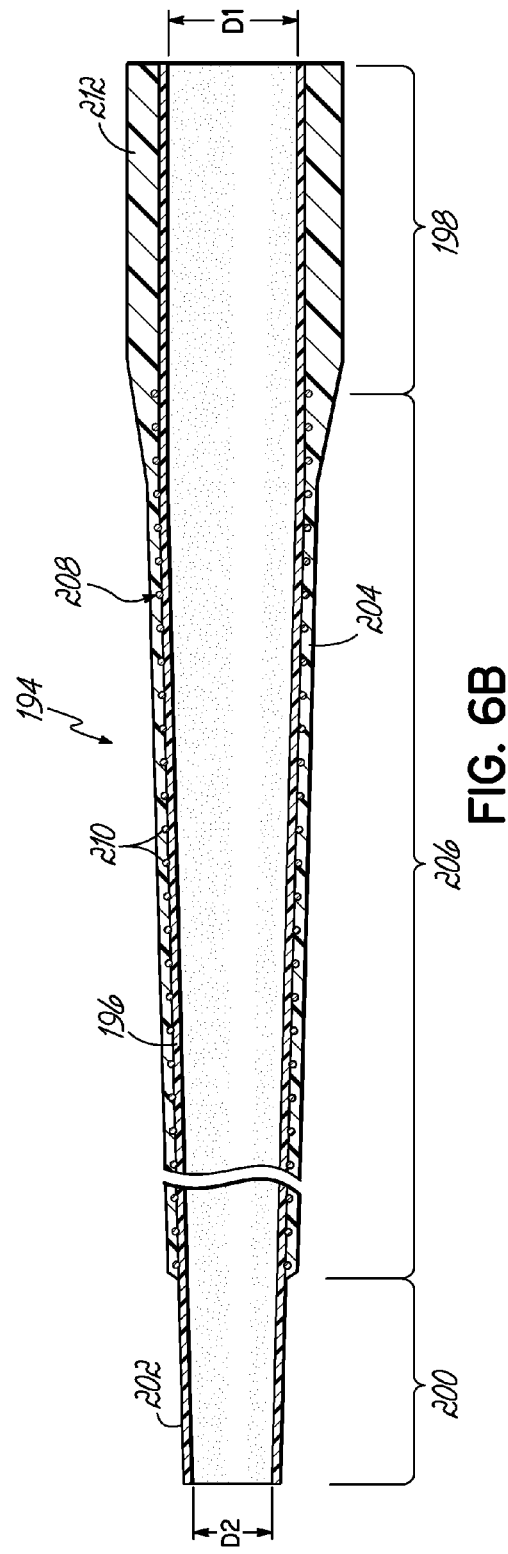

CANNULA LINED WITH TISSUE IN-GROWTH MATERIAL AND METHOD OF USING THE SAME

CROSS-REFERENCE TO RELATED APPLICATION

This application claims the benefit of U.S. Provisional Patent Application Ser. No. 61/303,351, filed on Feb. 11, 2010, the disclosure of which is incorporated by reference herein, in its entirety.

TECHNICAL FIELD

The present invention relates generally to cannulae, and more specifically to cannulae for use with the pump of a circulatory assist system.

BACKGROUND

The human heart is the muscle that is responsible for pumping blood throughout the vascular network. Veins are vessels that carry blood toward the heart while arteries carry blood away from the heart. The human heart consists of two atrial chambers and two ventricular chambers. Atrial chambers receive blood from the body and the ventricular chambers, which include larger muscular walls, pump blood from the heart. A septum separates the left and the right sides of the heart.

Various devices and methods have been utilized to assist the heart in blood circulation, particularly for patients having congestive heart failure (commonly referred to as heart disease), which is a condition that results in any structural or functional cardiac disorder that impairs the ability of the heart to fill with or pump blood throughout the body. These devices generally include a pump, which may reside in a subcutaneous pump pocket, and cannulae fluidically attaching the pump to the vascular network. One cannula is used to transmit oxygenated blood from the left side of the heart to the pump; another cannula is used to direct that blood from the pump to the arterial network.

Despite the benefits gained by assisting the heart with the implantable pump, issues may arise from the presence of the cannula within the vessel. The arteries and veins of the vascular network have a particular anatomical structure that includes three layers: the tunica externa, the tunica media, and the tunica intima, respectively from the outer most layer, inward. The tunica intima, which includes a combination of endothelial cells and the protein elastin, creates a biological barrier that performs several functions. One essential function is the maintenance of a smooth inner surface that resists clotting and promotes smooth blood flow. The endothelial cells secrete various regulatory compounds that aid processes, such as vasoregulation and coagulation. When a conventional cannula is positioned within a blood vessel, the polymer or urethane comprising the cannula, or the mere presence of the cannula itself, may physically and/or chemically perturb the endothelial cells of the tunica intima and induce a prothrombotic environment. Thrombus formations may wash into the implantable pump of the assist device causing pump failure or alternatively induce a thrombolic event, including stroke or kidney infarct. Accordingly, it would be beneficial to create an environment within the cannula that mimics the native biological structure and framework of the blood vessel to reduce the occurrence of thrombic events.

SUMMARY

In one illustrative embodiment, the invention is directed to a cannula for moving fluids between a pump and the circulatory system of a patient. The cannula includes a liner having an intermediate portion between a proximal portion and a distal portion, and a lumen extending between the proximal and distal portions. At least the intermediate portion of the liner is constructed from a tissue in-growth material for supporting the growth of endothelial cells. A jacket surrounds at least part of the liner.

In another illustrative embodiment, the invention is directed to a cannula for moving fluids between a pump and the circulatory system of a patient. The cannula includes a liner having an intermediate portion between a proximal portion and a distal portion, and a lumen extending between the proximal and distal portions. At least the intermediate portion of the liner is constructed from a tissue in-growth material for supporting the growth of endothelial cells. A reinforcing structure surrounds at least a part of the intermediate portion for resisting kinks along the length of the cannula. A jacket surrounds the reinforcing structure and at least part of the liner.

According to another illustrative embodiment, the invention is directed to an inflow cannula for moving fluids between the heart of a patient and a pump. The inflow cannula includes a liner having an intermediate portion between a proximal portion and a distal portion, and a lumen extending between the proximal and distal portions. At least the intermediate portion of the liner is constructed from a tissue in-growth material for supporting the growth of endothelial cells. A tip is coupled to the distal portion of the inflow cannula for securing the inflow cannula to a wall of the heart. A hub of the inflow cannula is coupled to the proximal portion of the inflow cannula and secures the inflow cannula to the pump.

In accordance with yet another illustrative embodiment, the invention is directed to an outflow cannula for moving fluids between a pump and an arterial structure of the circulatory system of a patient. The outflow cannula includes a liner having an intermediate portion between a proximal portion and a distal portion, and a lumen extending between the proximal and distal portions. At least the intermediate portion of the liner is constructed from a tissue in-growth material for supporting the growth of endothelial cells. A hub is coupled to the proximal portion of the outflow cannula for securing the outflow cannula to the pump. A distal end of the outflow cannula is configured to be coupled to the arterial structure.

A cannula delivery system is described in accordance with another illustrative embodiment of the invention. The cannula delivery system includes a delivery sheath and a dilator. The delivery sheath has a body with proximal and distal ends and a lumen extending between. The distal end of the body includes a balloon-expandable section having two states: a first state with a smaller diameter and a second state with a larger diameter. In the second state, the balloon-expandable section is configured to receive a cannula and to move relative thereto. The dilator has a distally-positioned inflation member that is positioned within the balloon-expandable section of the delivery sheath. Inflation of the distally-positioned inflation member expands the balloon-expandable section from its first state to its second state.

Another illustrative embodiment of the invention is directed to a method of percutaneously inserting a cannula into a tissue. The method includes directing a delivery sheath through a puncture in the tissue. The delivery sheath has a body with proximal and distal ends and a lumen extending between. The distal end of the body includes a balloon-expandable section in a first, collapsed state. An inflation member positioned within the balloon-expandable section is inflated and causes expansion of the balloon-expandable section from the first, collapsed state to a second, expanded state. This dilates the puncture in the tissue. The inflation member is deflated and retracted from the delivery sheath so that a cannula may be directed into and through the lumen of the delivery sheath to the balloon-expandable section. The delivery sheath is retracted, relative to the cannula, which extends through the dilated puncture.

In another illustrative embodiment, the invention is directed to a cannula assembly that includes a flexible cannula body, a tip, an anchor, and a porous polymeric structure. The tip is coupled to a distal portion of the flexible cannula body and the anchor is coupled to the tip. The anchor is configured to be deployed from a contracted state to an expanded state. In the expanded state, the anchor engages at least one side of the heart tissue and resists movement of the cannula in at least one direction. The porous polymeric structure is coupled to an outer surface of the tip, adjacent to the anchor, and is configured to facilitate tissue in-growth.

BRIEF DESCRIPTION OF THE DRAWINGS

FIG. 4A is a disassembled, side-elevational view of an exemplary embodiment of a cannula delivery system and including a delivery sheath, a dilator, and a guidewire.

FIG. 4B is an assembled, side-elevational view of the cannula delivery system of FIG. 4A, shown in a collapsed state.

FIGS. 4C-4E are enlarged, side-elevational views of an exemplary method of advancing the assembled cannula delivery system of FIG. 4B across a tissue wall.

FIG. 6A is a side-elevational view of one exemplary embodiment of an outflow cannula for use with the circulatory assist system, shown in partial cross-section.

FIG. 6B is a side-elevational view of an alternative embodiment of an outflow cannula for use with the circulatory assist system, shown in partial cross-section.

DETAILED DESCRIPTION

Figure 1:
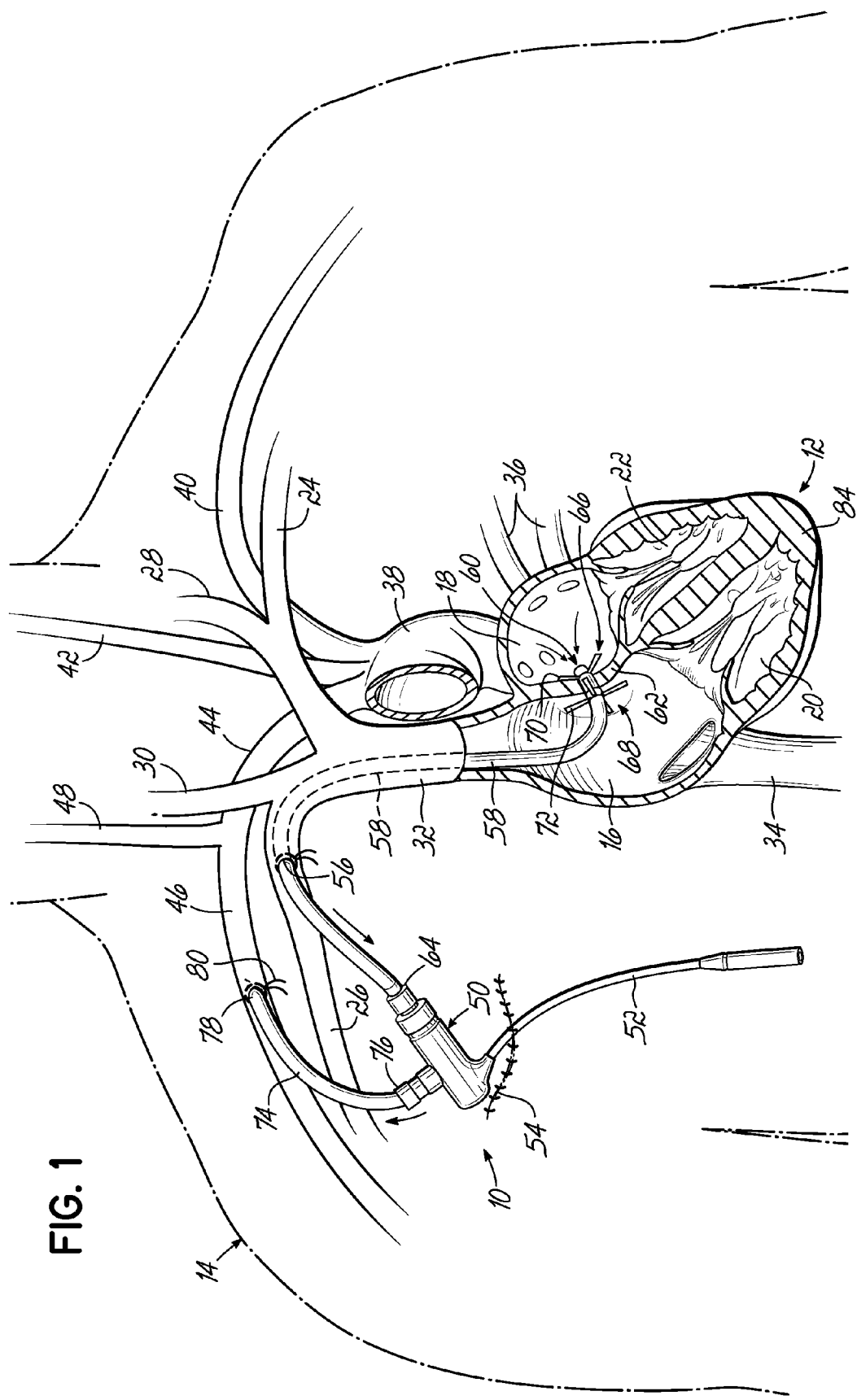
FIG. 1 is a diagrammatic view of a circulatory assist system, with the heart shown in cross-section.

FIG. 1 illustrates an implanted circulatory assist system 10. For illustrative purposes, certain anatomy is shown including the heart 12 of a patient 14 having a right atrium 16, a left atrium 18, a right ventricle 20, and a left ventricle 22. Blood from the left and right subclavian veins 24, 26 and the left and right jugular veins 28, 30 enters the right atrium 16 through the superior vena cava 32 while blood from the lower parts of the body enters the right atrium 16 through the inferior vena cava 34. The blood is pumped from the right atrium 16, to the right ventricle 20, and to the lungs (not shown) to be oxygenated. Blood returning from the lungs enters the left atrium 18 via pulmonary veins 36 and is then pumped into the left ventricle 22. Blood leaving the left ventricle 22 enters the aorta 38 and flows into the left subclavian artery 40, the left common carotid 42, and the brachiocephalic trunk 44 including the right subclavian artery 46 and the right common carotid 48.

With respect to the implanted circulatory assist system 10, two cannulae extend between the vascular network and a pump 50, which may be any implantable or extracorporeal pump that may be radially- and/or axially-driven. Those skilled in this art, however, recognize that other types of pumps may be used in other embodiments but may include pumps such as those described in U.S. patent application Ser. No. 11/627,444, published as 2007/0197854, which is incorporated herein by reference in its entirety.

A cable 52 may extend transdermally from the pump 50 to a position in the abdomen where the cable 52 exits the patient 14 and connects to a power supply (not shown). Suitable power supplies may be any universal-type power supply that sends power to the pump 50 via the cable 52 and may include, but is not limited to, a rechargeable battery pack.

As illustrated, the physician may position the implantable pump 50 at least subcutaneously and, optionally, submuscularly in a pump pocket 54 located near a venous access site 56, or alternatively, maintain the pump 50 externally.

A first, inflow cannula 58 extends from a tip 60 within the left atrium 18, across the intra-atrial septum 62, and percutaneously to the venous access site 56, shown here to be in the right subclavian vein 26. The inflow cannula 58 extends through the venous access site 56 to an input port 64 of the pump 50. Though not shown, the inflow cannula 58 may alternatively be surgically connected to either the left or right side the heart 12 and extend to the pump 50 through the thoracic cavity in a manner described generally in U.S. patent application Ser. No. 11/846,839, published as 2008/0076959, the disclosure of which is incorporated herein in its entirety. The tip 60 may have various shapes, including those described in U.S. patent application Ser. No. 12/392,623 (published as 2009/0182188) and Ser. No. 12/256,911 (published as 2009/0112050), the disclosures of which are also incorporated herein by reference in their entireties. In any event, the illustrative tip 60 includes first and second deployable anchors 66, 68, each including a plurality of struts 70, 72, respectively, for securing the tip 60 to the intra-atrial septum 62.

A second, outflow cannula 74 extends from an output port 76 of the pump 50 to an arterial access site 78, illustrated here in the right subclavian artery 46. The outflow cannula 74 may be secured at the arterial access site 78 by one or more sutures 80 or one or more anastomotic connectors, such as those taught in U.S. patent application Ser. No. 12/829,425, the disclosure of which is incorporated herein by reference, in its entirety.

Alternatively, the physician may surgically position another embodiment of the tip 82 through the apex 84 of the heart 12 and into the left ventricle 22. The tip 82, which is described in greater detail in U.S. patent application Ser. No.

13/025,757 filed on even date herewith and incorporated herein by reference in its entirety, includes one or more openings 86 that extend proximally from a distal tip end 88. The openings 86 permit the flow of blood from the left ventricle 22 into a lumen 90 (FIG. 3) of the inflow cannula 58 even in the event that the distal tip end 88 becomes obstructed with tissue from within the left ventricle 22. Inclusion of this particular embodiment of the tip 82 is not required, but instead may be replaced with other tips that are suitable for insertion through the apex 84. The outflow cannula 74 may extend from the pump 50 to an arterial access site 78' within the ascending aorta 38. Other arrangements, though not shown, may also be used in accordance with the particular need and to accommodate the unique anatomy of the patient 14.

Figure 1A:
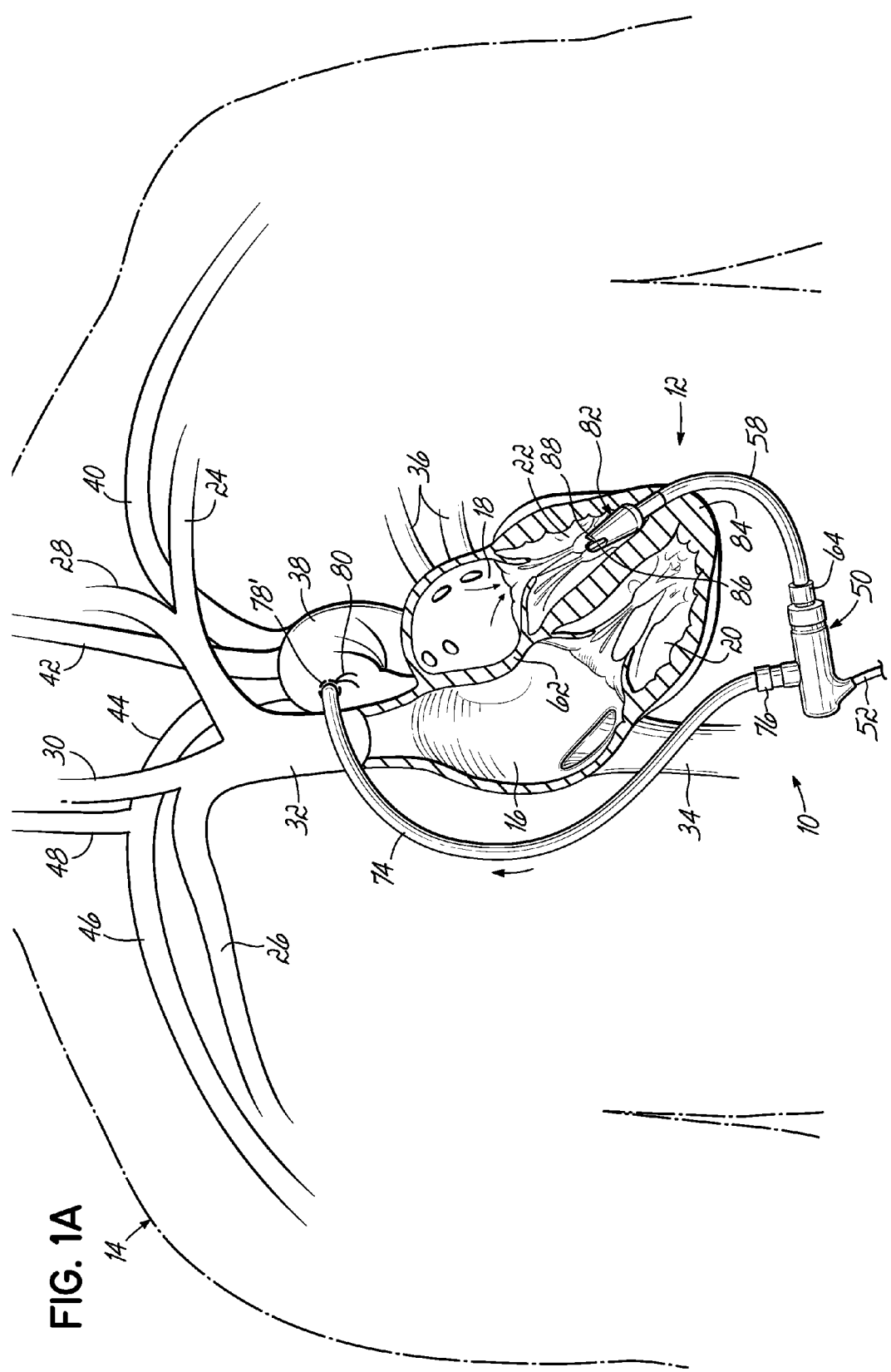
FIG. 1A is a diagrammatic view of an alternate position of the circulatory assist system, with the heart shown in cross-section.
Figure 2:
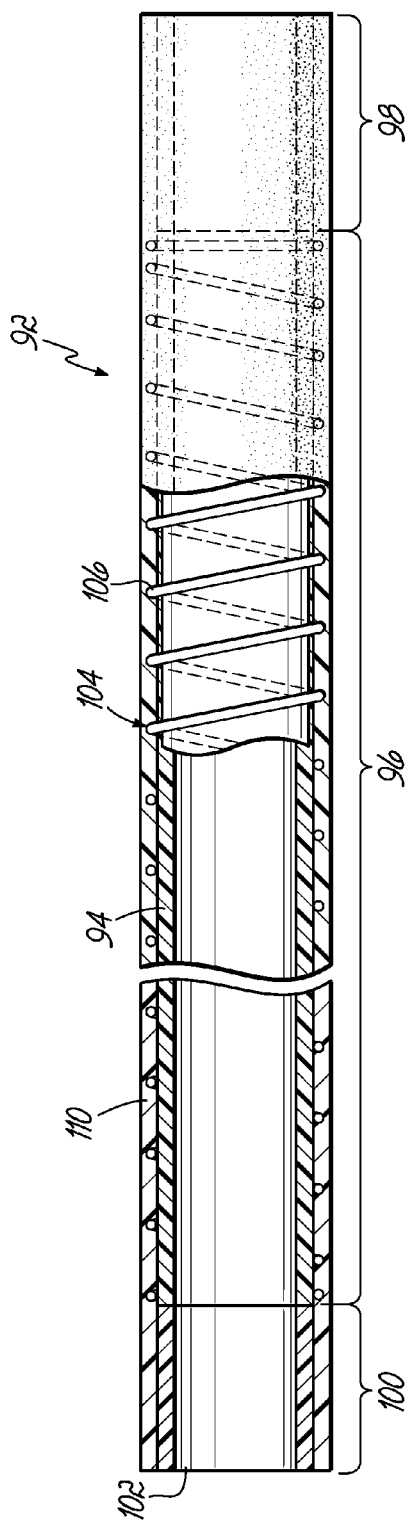
FIG. 2 is a side-elevational view of one exemplary embodiment of a cannula, shown in partial cross-section.

Use of known, conventional cannula with the circulatory assist system 10 of FIGS. 1 and 1A may induce a prothrombotic environment. Therefore, the inflow cannula 58 or the outflow cannula 74 or both may be constructed in a manner that mimics the native biological structure and framework of blood vessels. Accordingly, and with reference now to FIG. 2, one such biocompatible cannula 92 structure is described in greater detail.

The liner 94 includes an intermediate portion 96 between a proximal portion 98 and a distal portion 100, with a lumen 102 extending therethrough. In some embodiments, the portions 96, 98, 100 of the liner 94 are constructed as a unitary structure that extends the full length of the biocompatible cannula 92. Alternatively, a majority of the length of the liner 94, i.e., the intermediate portion 96, is constructed from a tissue in-growth material while the proximal and distal portions 98, 100 include other materials as described below. The tissue in-growth material may be a porous polymeric material, such as expanded polytetrafluoroethylene (ePTFE), a woven polyester fabric tubing (e.g., DACRON brand of polyester fabric), velour, or like materials that create a scaffolding to which endothelial cells adhere and create a biostable environment within the cannula 92 in a manner described in greater detail below. Alternatively, the proximal and distal portions 98, 100 are constructed from a polymeric material and are added to the respective ends of the intermediate portion 96. Suitable polymeric materials for the proximal and distal portions 98, 100 may include elastomeric materials, such as polyurethanes or silicones, that are capable of connecting the cannula 92 to the pump 50 (FIG. 1) or to a distally-positioned cannula tip 60 (FIG. 1).

One or more portions of the liner 94 may be surrounded by a reinforcing structure 104 to resist the collapse or kinking of the cannula 92 while providing the desired level of flexibility; however, the reinforcing structure 104 would generally not extend to the proximal and distal portions 98, 100 so that these portions may remain flexible for the attachment to the tip 60 (FIG. 1) or the pump 50 (FIG. 1), as appropriate. The reinforcing structure 104 may be constructed as a coil 106 (shown) or a braid 108 (FIG. 6A) from metallic materials, such as stainless steel, chromium cobalt, or nickel titanium, or from a rigid polymeric material.

The liner 94 and the reinforcing structure 104 are covered with a jacket 110, which may be constructed from a polymeric material. With a heat melt process, the liner 94 bonds to the polymeric material of the jacket 110 and encapsulates the reinforcing structure 104. In some embodiments, an outer surface of the liner 94 may be coated with a thin layer of solution grade polyurethane or a silicone. This low viscosity coating facilitates the introduction of the polymeric material of the jacket 110 into the structure of the porous polymeric material of the liner 94. For urethane-based constructions, the bonding between the liner 94 and the jacket 110 occurs through a melt process; for silicone-based constructions, the bonding between the liner 94 and the jacket 110 occurs through a cross-linking process during the curing cycle of construction. The proximal end of the jacket 110 may be structured as desired to accommodate the coupling of the cannula 92 to the pump 50 (FIG. 1). This may include a flared or expanded section to form a hub and is described in greater detail below with reference to FIGS. 3 and 5A.

It would be understood that in those embodiments where the liner 94 is constructed as a unitary structure, the jacket 110 would bond directly to the tissue in-growth material of the liner 94.

Figure 3:
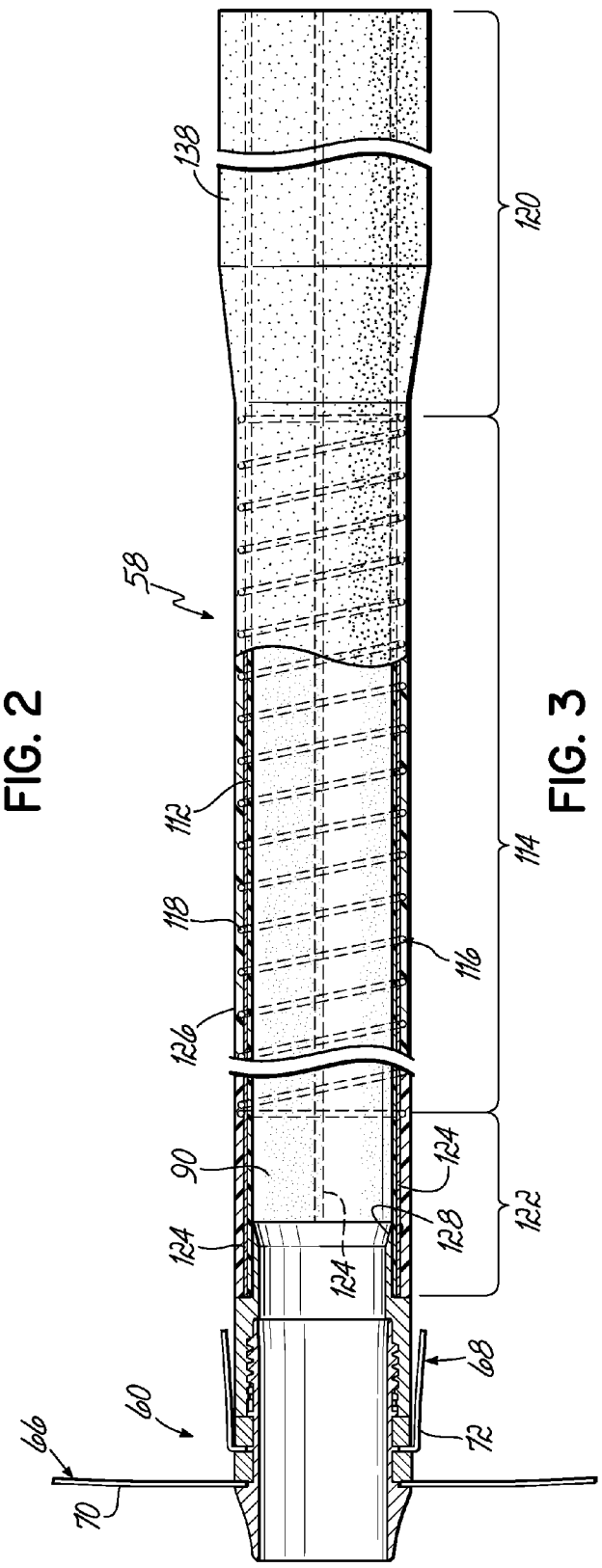
FIG. 3 is a side-elevational view of one exemplary embodiment of an inflow cannula for use with the circulatory assist system, shown in partial cross-section.

FIG. 3 illustrates the inflow cannula 58 of FIG. 1, which has been constructed in a manner that is consistent with one or more embodiments of the invention. As shown, the liner 112 is constructed as a unitary structure of tissue in-growth material. The intermediate portion 114 of the liner 112 includes a reinforcing structure 116 (shown as a coil 118) while the proximal and distal portions 120, 122 do not include the reinforcing structure 116. As shown in phantom, the inflow cannula 58 may also include one or more longitudinal strengtheners 124 that extend, at least partially along the intermediate portion 114 between the liner 112 and the reinforcing structure 116, if present, and/or the jacket 126. The longitudinal strengtheners 124, in addition to the reinforcing structure 116, provide better longitudinal control over the length of the inflow cannula 58. Any semi-flexible or flexible material may be used for constructing the longitudinal strengtheners 124, including for example, non-absorbable suture materials such as nylon or polypropylene; however, metallic materials, alloys, and/or other materials may also be used.

The struts 70, 72 of the anchors 66, 68 of the tip 60 may be constructed by chemically etching the structure from a sheet of a superelastic material, electropolishing the etched structure to remove rough edges generated during the formation process, and then heating the structure to a superelastic state. Because of the superelastic state, the anchors 66, 68 may be deployable from a folded position (see the second anchor 68) to a deployed position that extends radially from the tip 60 (see the first anchor 66). It would be readily appreciated that while four struts 70, 72 per anchor 66, 68 are shown, any number of struts may be used.

In some embodiments, though not specifically shown, the struts 70, 72 are encapsulated within a porous polymeric structure that provides a larger surface for engaging the tissue of the vascular structure than the plurality of struts 70, 72 alone when the tip 60 is inserted into the vascular structure. Additionally, the porous polymeric structure allows for tissue in-growth, wherein tissue from the wall of the vascular structure may grow and embed within the porous polymeric structure to provide greater structural stability and sealing capacity. Further details of the first and second anchors 66, 68 may be found in U.S. patent application Ser. No. 12/256,911.

The tip 60 may be constructed from a polished titanium or other suitable material and have a design that reduces fluidic turbulence and the risk of thrombosis formation. The tip design may also facilitate the coupling of the tip 60 to the distal portion 122 of the liner 112 of the inflow cannula 58. For example, in some embodiments, the proximal end of the tip 60 may include one or more barbs 128 to provide resistance against undesired removal of the tip 60 from the inflow cannula 58. The tip 60 may additionally, or alternatively, be coupled and/or secured to the inflow cannula 58 by a suture tie 130 (FIG. 5A) that is encapsulated by a UV adhesive 132 (FIG. 5A), which is cured in a known manner. The suture tie 130 is operable to cinch and secure the inflow cannula 58 onto the tip 60. In yet other embodiments, the tip 60 may be additionally, or alternatively, secured to the inflow cannula 58 by a band 134 (FIG. 5B) that is operable to swage or crimp the cannula 58 onto the tip 60. Optionally, the band 134 (FIG. 5B) may be constructed from a material that would enable a surgeon to remotely determine the location of the tip 60, including but not limited to radiopaque materials, such as platinum-iridium, stainless steel, tungsten, or tantalum. Such remote visualization may be accomplished in any known manner, such as X-ray or real time fluoroscopy. The band 134 (FIG. 5B) may be further covered or encapsulated with a cover 136 that is constructed of the tissue in-growth material, consistent with any of the embodiments described herein.

The proximal end of the inflow cannula 58 may be expanded to form a hub 138 that is configured to be coupled to the inflow port 64 (FIG. 1) of the pump 50 (FIG. 1).

The inflow cannula construction with the tissue in-growth material allows for the attachment of endothelial cells from the blood flowing through the lumen 90. Once the endothelial cells attach, they may undergo mitosis and proliferate to cover the length of the liner 112 that is constructed from the tissue in-growth material. This endothelial cell growth creates a biostable layer that more accurately replicates the native environment of a blood vessel. With the biostable layer, there is a reduction in perturbations that would induce endothelial generation of a prothrombotic environment. Accordingly, there is a reduction of thrombus formations that in return decreases the occurrence of pump failures.

Figure 3A:
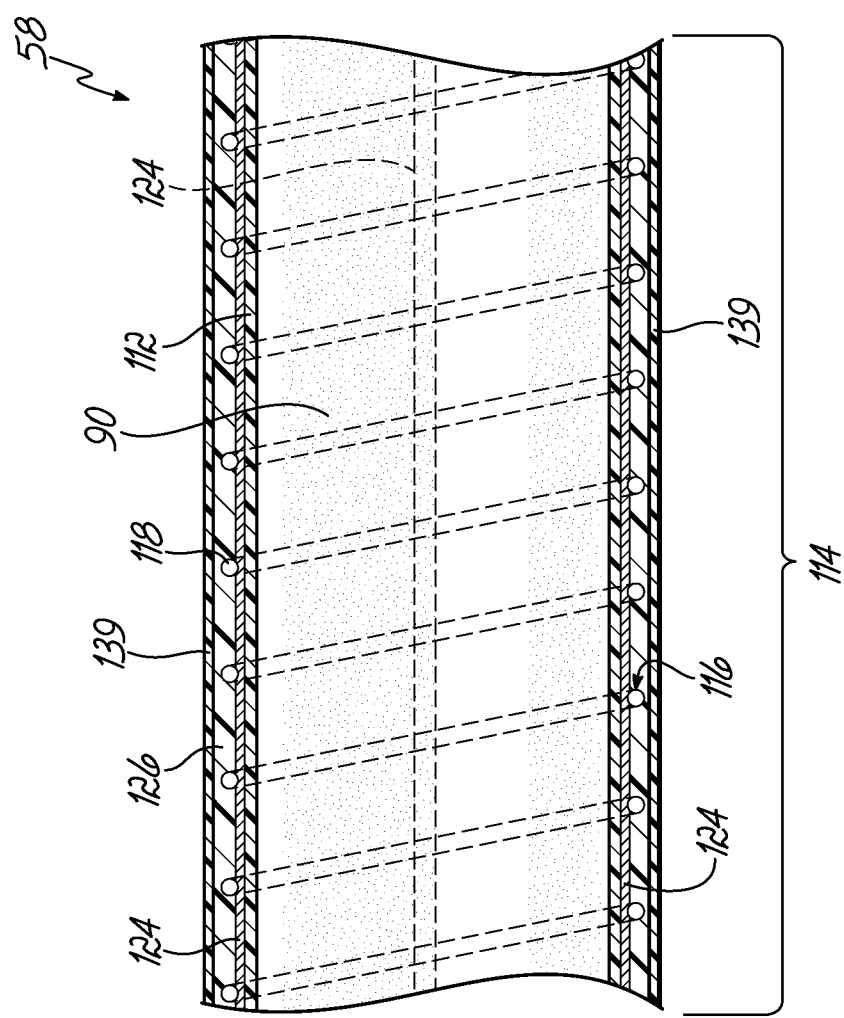
FIG. 3A is an enlarged and fragmented side-elevational view of another embodiment of an inflow cannula, shown in cross-section.

FIG. 3A illustrates an alternate embodiment of the inflow cannula 58. More specifically, an outer layer 139 constructed from a tissue in-growth material is added to the outer surface of the jacket 126. The tissue in-growth material may be a porous polymeric material, such as expanded ePTFE, a woven polyester fabric tubing (e.g., DACRON brand of polyester fabric), velour, or like materials that create a scaffolding to which cells adhere. The outer layer 139 extends over the intermediate portion 114 of the inflow cannula 58, but may also extend over the distal and proximal portions 122, 120, if desired. Inclusion of this outer layer 139 is useful when the inflow cannula 58 resides within the vascular network, for example as shown in FIG. 1, and particularly where blood flow may stagnate due to the inflow cannula 58. As the inflow cannula 58 extends through the right subclavian vein 26 and the superior vena cava 32 as shown in FIG. 1, there may be a tendency for the inflow cannula 58 to contact an inner surface of the venous wall, particularly along curving portions of the walls. Those areas in which the inflow cannula 58 contacts the venous wall will experience reduced blood flow, i.e., stagnation, which may then lead to thrombus formation. By including the tissue in-growth material as the outer layer 139 to the inflow cannula 58, a biostable environment is created that replicates the vascular environment and reduces perturbations that would otherwise generate a prothrombotic environment. While the outer layer 139 is illustrated here with the inflow cannula, it would be readily appreciated that the outer layer 139 may be included on one or more portions of the outflow cannula 74 if desired.

The inflow cannula 58 may be delivered in a surgical method, such as those described in U.S. patent application Ser. No. 11/846,839, or in a percutaneous manner, such as described in U.S. patent application Ser. No. 12/256,911. Percutaneous delivery may proceed by way of a delivery system 140, which is illustrated in FIG. 4A. The delivery system 140 includes a delivery sheath 142 having a body 144 that may be constructed as three thin-layer walls, though it is illustrated as a single-walled structure herein. An exterior layer may be constructed of polyurethane, Nylon-11, Nylon-12, or PEBAX; an interior layer can be a liner made from an ePTFE, urethane, or Nylon with hydrogel coating; and a mid-layer can be constructed from a braided material, such as stainless steel wire, Nitinol, or polyeretherketones (PEEK) fibers to provide structural stability to the delivery sheath 142. The interior layer or an interior liner may be extruded and placed upon a mandrel with the mid-layer and the exterior layer respectively formed or otherwise placed over the interior layer. Polyurethane is then placed over the entire assembly and heat shrink wrapped over the tube for stability. Alternatively, the delivery sheath 142 may be laminated by a reflow process. In some instances, a superelastic coil (not shown) may be included around the delivery sheath 142 to increase the rigidity of the delivery sheath 142. Alternatively, a metallic braid (not shown) could be included around the delivery sheath 142. A polymeric layer may surround the superelastic coil (not shown) to reduce friction as the delivery sheath 142 moves within the vascular network.

A distal end of the delivery sheath 142 may include a balloon-expandable section 146, which may be a multilayer construction having two states: a first, non-expanded state (shown in FIG. 4B) and a second, expanded state (shown in FIG. 4A). The multilayer construction may be formed from lower durometer materials such as PEBAX brand of polymers or polyurethane for compliant or easy inflation or from higher durometer materials such as nylon or polyethylene terephthalate (PET) for a balloon-expandable section 146 that is more resistant to inflation. As an alternate configuration, the balloon expandable section 146 may be constructed using a porous polymeric material such as ePTFE, DACRON brand of polyester fabrics, or velour, as the inner and outer layers with a balloon expandable structure 148 sandwiched between the layers. The balloon expandable structure 148 may reside between the inner layer and the outer jacket in a manner that may be similar to a covered stent-like construction and may be constructed from a deformable material, such as a metallic alloy (e.g., stainless steel, or chromium cobalt, CrCo) or a rigid polymer, that aids in preventing the collapse of the delivery sheath 142 due to tissue recoil during insertion of the inflow cannula 58 (FIG. 1). One suitable balloon expandable structure 148 may be machined from a hypo-tube in a manner that is similar to the construction of a balloon-expandable stent. When the proximal support structure is used, the proximal section of the balloon expandable structure 148 may be coupled to the distal end of the superelastic coil (not shown).

A hub 150 is attached to the proximal end of the delivery sheath 142 by gluing, welding, or other means. The hub 150 may include a side port 152 having a conduit 154 that extends to a flush valve 156. Though not specifically shown, the hub 150 may include any suitable hemostatic seal for preventing the back-flow of bodily fluid and should not be limited to the structure illustrated herein.

A dilator 158, such as a balloon appliance, is backloaded through the hub 150 and into the lumen of the delivery sheath 142 to the balloon-expandable section 146 while in a deflated state. The dilator 158 may be any commercially-available balloon catheter and generally includes a catheter body 160 and an expandable distal portion 162, illustrated specifically herein as a balloon 164. In some embodiments, the length of the balloon 164 would be substantially similar to the length of the balloon-expandable section 146 of the delivery sheath 142 so that the balloon 164 need only be inflated once; however, in other embodiments where the length of the balloon-expandable section 146 exceeds the balloon 164, then multiple inflations/deflations may be necessary to ensure that the entire length of the balloon-expandable section 146 is fully expanded. Further, it would be understood that when the expanded diameter of the balloon 164 substantially matches the desired expanded diameter of the balloon-expandable section 146, then full inflation of the balloon 164 would result in the desired diameter of the balloon-expandable section 146; however, embodiments where partial inflation of a balloon having a diameter that is greater than the desired expanded diameter of the balloon-expandable section would also be acceptable. The catheter body 160 and a hub 166 of the catheter body 160 may include a multi-lumen tube or multiple tubes such that one tube or lumen receives a guidewire 168 and another tube or lumen facilitates inflation/deflation of the balloon 164. The guidewire 168, itself, may also include a hub 170 configured to facilitate movement of the guidewire 168 within the vascular system.

The delivery system 140, including the guidewire 168, is shown in FIG. 4B such that the dilator 158 extends through the lumen of the delivery sheath 142 and the balloon-expandable section 146 is compressed, typically by crimping, onto the balloon 164 while in its non-expanded, or collapsed, state.

Figure 4E:
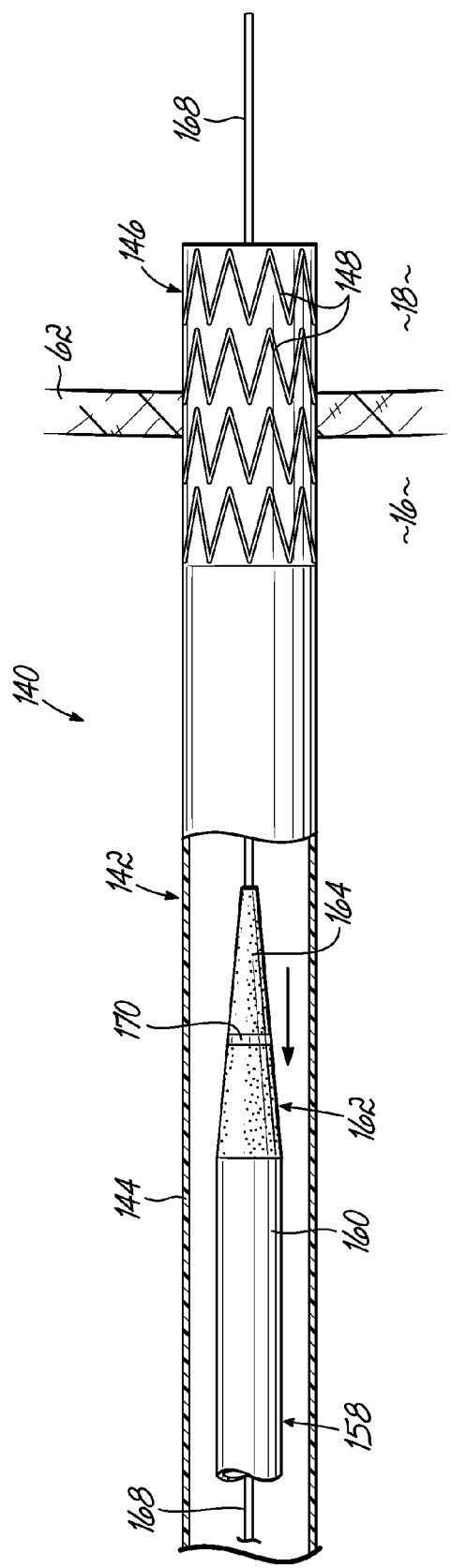

Use of the delivery system 116 may proceed, as illustrated in FIGS. 4C-4E with reference also to FIG. 1, by advancing the guidewire 168 to the surgical site for implanting the inflow cannula 58. In the particular illustrative embodiment, the guidewire 168 may be inserted through the venous access site 56 at the right subclavian vein 26 and advanced through the superior vena cava 32 and into the right atrium 16. From the right atrium 16, the guidewire 168 may puncture the intra-atrial septum 62 and enter the volume of the left atrium 18. While not shown, it would be readily understood that the procedure may also proceed by way of a transseptal needle that is then exchanged with the guidewire 168.

The delivery sheath 142 with the dilator 158 may then be advanced over the guidewire 168 and to the right atrial side of the intra-atrium septum 62. Because the balloon-expandable section 146 of the delivery sheath 142 and the balloon 164 are both collapsed, and thereby have a small profile, the delivery system 140 may advance over the guidewire 168, through the puncture, and into the left atrium 18. The tapered shape of the balloon-expandable section 146 dilates the puncture and facilitates insertion of the delivery sheath 142 through the intra-atrial septum 62. Positioning of the delivery system 140 may be facilitated by in vivo localization of one or more marker bands 170 that are positioned on the dilator 158 (refer to FIG. 4E), and that are constructed from a radiopaque material and visualized as described above.

As shown in FIG. 4D, with the delivery sheath 142 inserted through the intra-atrial septum 62, the balloon 164 of the dilator 158 may be inflated, in a known manner, causing expansion of the balloon 164 against an inner surface of the balloon-expandable section 146 of the delivery sheath 142. The balloon-expandable section 146 also expands, thereby further dilating the puncture.

FIG. 4E illustrates the deflation and retraction of the balloon 164 after one or more inflation/deflation steps ensure full expansion of the balloon-expandable section 146. The balloon-expandable section 146 retains its fully expanded state and resists recoil of the tissue during passage of the inflow cannula 58.

Figure 4F:
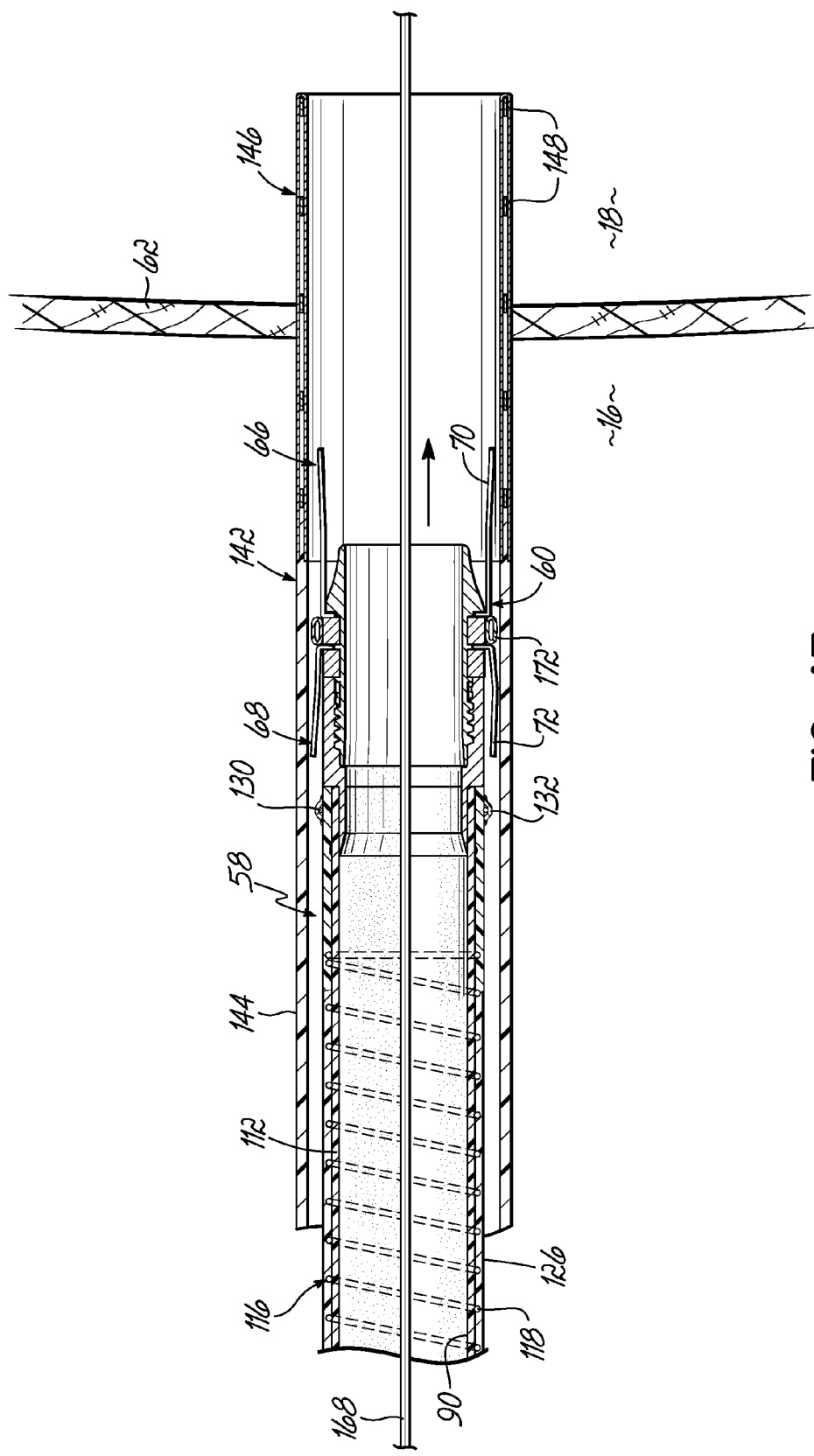
FIG. 4F is an enlarged, side-elevational view of an exemplary method of advancing an inflow cannula through the delivery sheath positioned through the tissue wall.

FIG. 4F illustrates the inflow cannula 58, which is advanced through the lumen of the delivery sheath 142 to the intra-atrial septum 62. Deployment of the anchors 66, 68 on the tip 60 may proceed in the manner that was described in detail in U.S. patent application Ser. No. 12/256,911. Briefly, the inflow cannula 58 with the tip 60 is advanced beyond the delivery sheath 142 and into the volume of the left atrium 18 such that the first anchor 66, unrestrained by the delivery sheath 142, is deployed and expands radially outward. The delivery sheath 142 with the inflow cannula 58 are retracted such that the first anchor 66 resides adjacent the intra-atrial septum 62 within the left atrium 18. While maintaining the position of the inflow cannula 58, the delivery sheath 142 is then further retracted, thereby deploying the second anchor 68 such that the tip 60 spans the intra-atrial septum 62 and the anchors 66, 68 reside on opposing sides of the intra-atrial septum 62, as shown in FIG. 1.

Figure 5A:
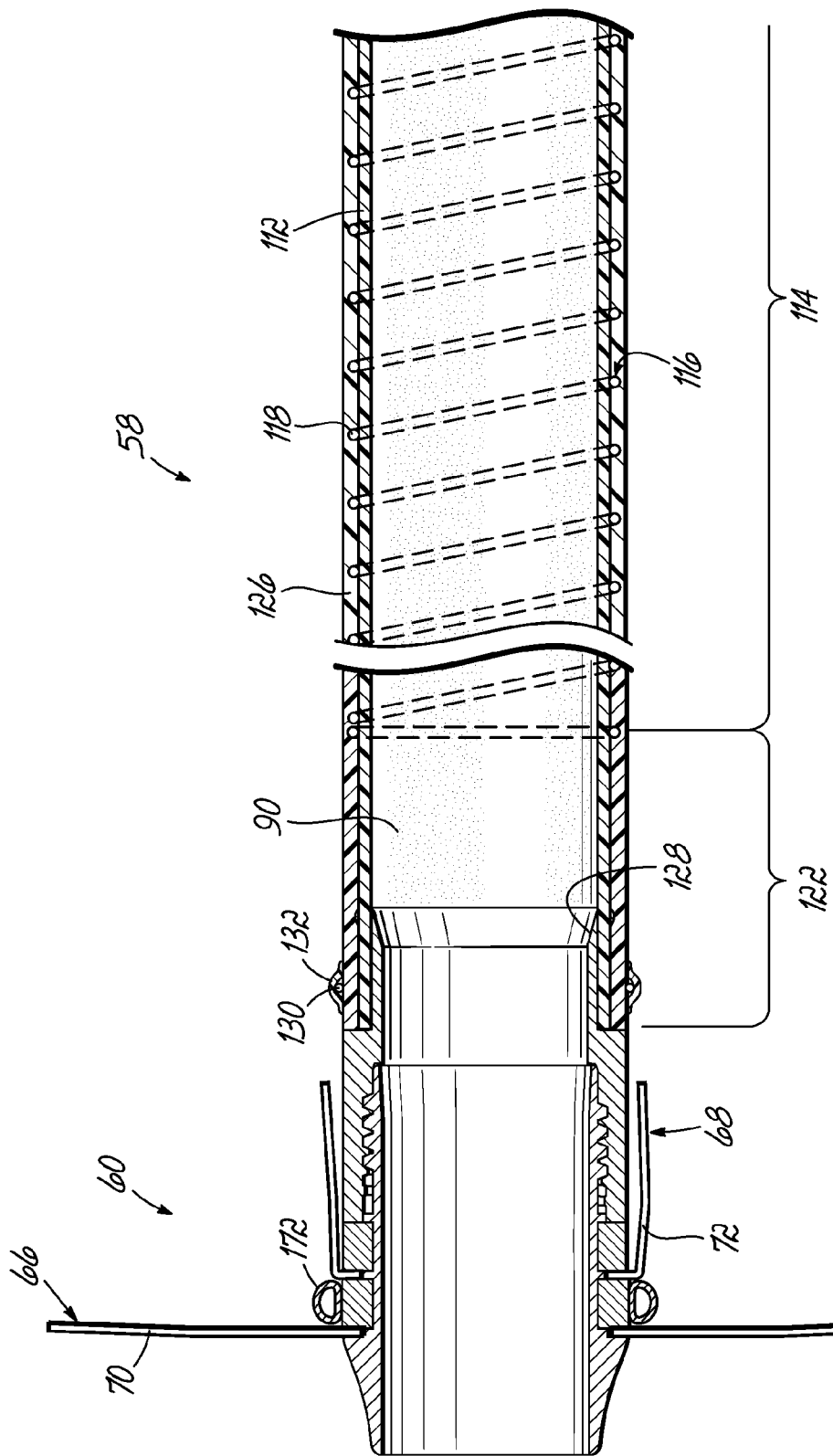
FIG. 5A is a side-elevational view of another embodiment of an inflow cannula having a tip coupled to the distal end thereof.
Figure 5B:
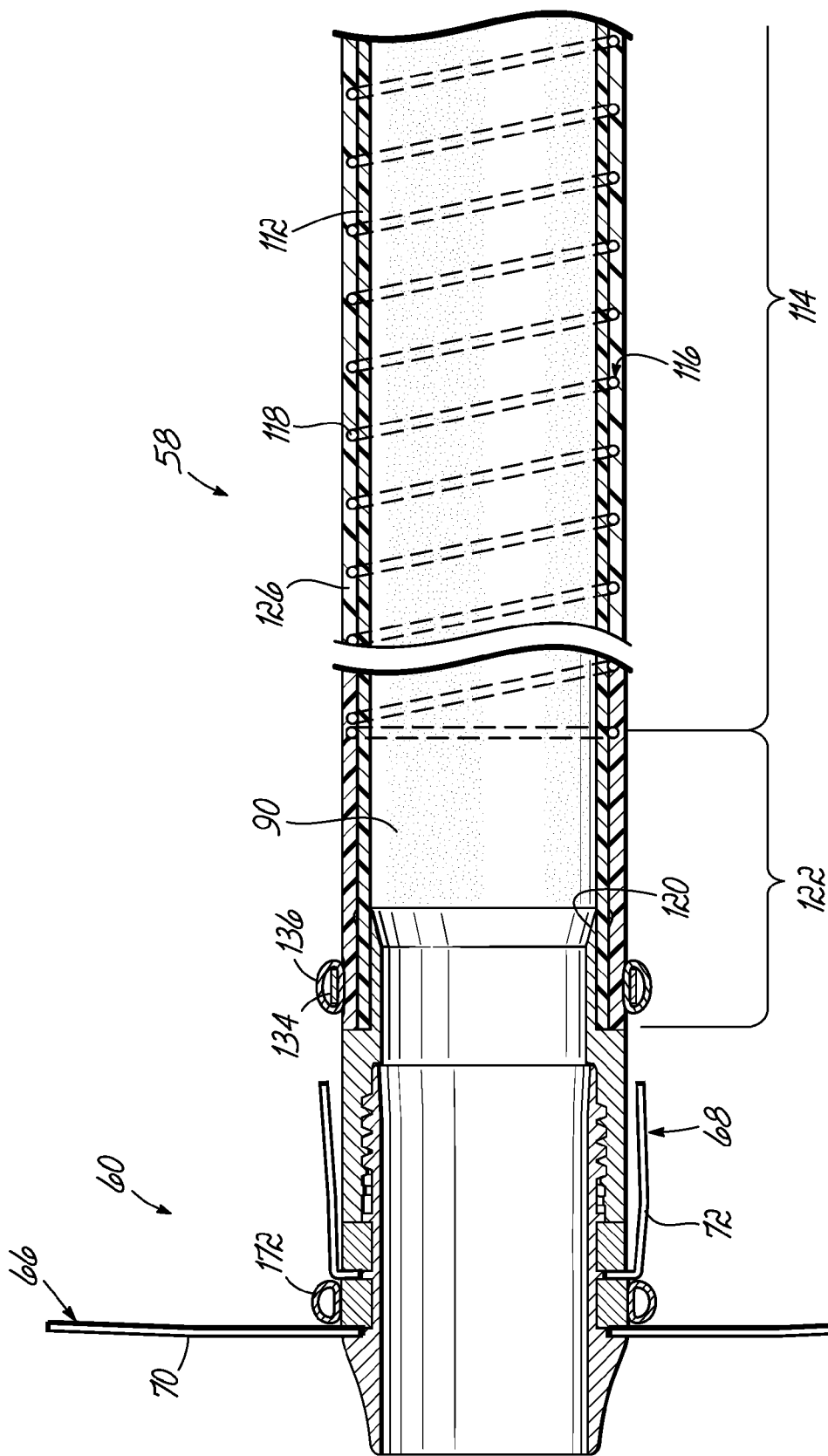
FIG. 5B is a side-elevational view of yet another embodiment of an inflow cannula having a tip coupled to the distal end thereof.

The inflow cannula 58 illustrated in FIGS. 5A and 5B includes a tissue in-growth member, such as a band 172. While the band 172 covers only a portion of an outer surface of the tip 60, other forms of tissue in-growth members may be used instead, and may cover the entire outer surface of the tip 60. The band 172 is annular and resides along the circumferential surface between the first and second anchors 66, 68. The band 172 may be formed of any suitable material that promotes tissue in-growth, such as any of the materials discussed herein for that purpose. In some embodiments, it may be beneficial to increase the distance between the first and second anchors 66, 68 to accommodate the band 172. After the tip 60 is secured to the intra-atrial septum 62 (FIG. 1), tissue of the septum 62 (FIG. 1) may at least partially grow into the material comprising the band 172 further securing the tip 60 to the septum 62 (FIG. 1). In yet other embodiments, the material comprising the band 172 may include a coating or otherwise be infused with a material that promotes healing of the tissue comprising the intra-atrial septum 62 (FIG. 1) at the surgical site. The coating may include a prothrombotic coating or a coating of calcium phosphate ($Ca_3(PO_4)_2$) to further promote tissue in-growth.

Turning now to FIG. 6A, the outflow cannula 74 of FIG. 1, which has been constructed in a manner that is consistent with one or more embodiments of the invention, is described in greater detail. While the liner 176 of the outflow cannula 74 is illustrated as a unitary structure, this is not necessary. The intermediate portion 178 of the liner 176 includes the braid 108 as the reinforcing structure 180 for kink resistance; however, a coil 106 (FIG. 2) or other suitable structure may alternatively be used. Furthermore, the reinforcing structure 180, as illustrated, does not extend over the proximal and distal portions 182, 184 to maintain flexibility of these portions; however, this should not be considered necessary.

The distal portion 184 of the liner 176 extends distally beyond the jacket 186 and is constructed from a thicker diameter of material such that the outer diameter of the liner 17 at the distal portion 184 is substantially similar to the outer diameter of the jacket 186 over the intermediate portion 178 to form a protruding section 188. In this way, the protruding section 188 may be used to create an anastomosis connection with the arterial structure, shown herein as the right subclavian artery 46 (FIG. 1); however, it would be understood by one skilled in the art that the protruding section 188 is not necessary and that a tip with an anchor, suture, or other means may be used for attaching the outflow cannula 74 to the arterial structure.

The proximal end of the outflow cannula 74 may be expanded to form a hub 190 that is configured to be coupled to the outflow port 76 (FIG. 1) of the pump 50 (FIG. 1).

The outflow cannula construction with the tissue in-growth material allows for the attachment of endothelial cells from the blood flowing through a lumen 192 of the outflow cannula 74. Again, once the endothelial cells attach, undergo mitosis, and proliferate to cover the length of the liner 176 constructed from the tissue in-growth material, a biostable layer is created that more accurately replicates the native environment of a blood vessel. With the biostable layer, there is a reduction in perturbations that would induce endothelial generation of a prothrombotic environment. Accordingly, there is a reduction of thrombus formations leading to decreases in the occurrence of outflow-cannula-induced thrombolic events, i.e., kidney infarct and/or stroke.

FIG. 6B illustrates an alternate embodiment of an outflow cannula 194 having a liner 196 that includes a tapered diameter such that the proximal portion 198 of the liner 196 has a lumen of a first diameter, D1, that is generally larger than the lumen of a second diameter, D2, of the distal portion 200 of the liner 196. This configuration is particularly beneficial when a larger diameter is required for attachment to the pump 50 (FIG. 1) and a smaller diameter is desired at the vessel. As illustrated herein, the smaller diameter distal portion 200 is constructed as a protruding section 202 that is similar to the construction described above. As shown in the instant embodiment, the protruding section 202 need not be constructed to match the outer diameter of the jacket 204 but, instead, may maintain the same diameter for the length of the outflow cannula 194.

The tapered cannula may have a D1 that ranges from about 6 mm to about 10 mm and a D2 that ranges from about 3 mm to about 7 mm. Also, while the outflow cannula 194 has been shown herein as including a taper that extends over the full length of the outflow cannula 194, other configurations may also be used, for example, a taper that extends only between the intermediate portion 206 and the distal portion 200.

As noted above, the outflow cannula 194 may include a reinforcing structure 208, shown as a coil 210, over at least the intermediate portion 206 of the liner 196. The proximal end of the outflow cannula 194 may also be expanded to form a hub 212.

Once the cannulae 58, 74 are positioned and coupled to the pump 50, the circulatory assist system 10 may be used to aid the heart 12 in pumping the patient's blood through the vascular network as was shown in FIG. 1. Depending on the cardiac output of the patient 14, a portion of blood flow will proceed in the native manner with oxygenated blood traveling from the left atrium 18 into the left ventricle 22 to the aorta 38. From the aorta 38, blood moves into the left subclavian artery 40, the left common carotid 42, and the brachiocephalic trunk 44. Another portion of the blood flow will proceed along the artificial path by entering the inflow cannula 58 and traveling through the lumen 94 of the inflow cannula 58 to the pump 50. From the pump 50, blood flows through the outflow cannula 74 to the particular arterial structure.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A cannula for moving blood between a pump and the circulatory system of a patient, the cannula comprising:
    a liner having a length and comprising an intermediate portion that extends for a majority of the length between a proximal portion and a distal portion, and a lumen extending between the proximal and distal portions, wherein at least the intermediate portion is constructed from a porous in-growth material that permits embedment therein of endothelial cells of blood flowing through the lumen to thereby reduce thrombus formations along an inner blood contacting surface of the cannula, the proximal portion is configured for connecting to the pump and the distal portion is configured for connecting to the circulatory system;
    a jacket fully encapsulating the liner; and
    a continuous outer layer bonded to and surrounding the jacket and extending along a full length of the intermediate and distal portions of the liner, the outer layer constructed from a porous in-growth material that permits embedment therein of endothelial cells of blood flowing along an outer blood contacting surface of the cannula to thereby reduce thrombus formations along the outer blood contacting surface.

2. The cannula of claim 1, wherein the porous in-growth material is an expanded polytetrafluoroethylene.

3. The cannula of claim 1, wherein the porous in-growth material is a porous polymeric material, a woven polyester material, or a velour.

4. The cannula of claim 1, wherein the proximal and distal portions of the liner are constructed from a polymer material.

5. The cannula of claim 4, wherein the polymer material is an elastomeric material.

6. The cannula of claim 5, wherein the elastomeric material is a polyurethane or a silicone.

7. The cannula of claim 1, wherein the jacket is constructed from a polymeric material and is bonded to the liner.

8. The cannula of claim 7, wherein an outer surface of the liner is coated with a compatible polyurethane or silicone solution before it is bonded to the jacket.

9. The cannula of claim 7, wherein the jacket is constructed from a polyurethane and is bonded to the liner by a melt process.

10. The cannula of claim 7, wherein the jacket is constructed from a silicone and is bonded to the liner by a cross-linking process.

11. The cannula of claim 1, wherein the distal portion is also constructed from the porous in-growth material.

12. The cannula of claim 11, wherein the diameter of porous in-growth material comprising the distal portion is larger than the diameter of the porous in-growth material comprising the intermediate portion.

13. The cannula of claim 1, wherein the liner is constructed as a unitary structure having the distal, intermediate, and proximal portions constructed from the porous in-growth material.

14. The cannula of claim 1 further comprising:
    a reinforcing structure surrounding at least a part of the intermediate portion of the liner for resisting kinks along the length of the cannula, wherein the liner and the jacket encapsulate the reinforcing structure.

15. The cannula of claim 14, wherein the reinforcing structure is a coil or a braid.

16. The cannula of claim 15, wherein the coil or braid is constructed from stainless steel, chromium cobalt, a superelastic material, or a rigid polymeric material.

17. The cannula of claim 1 further comprising:
one or more longitudinal strengtheners positioned between the liner and the jacket, extending, at least partially, between the proximal and distal portions.

18. The cannula of claim 17, wherein the one or more longitudinal strengtheners includes one or more suture strands.

19. The cannula of claim 1 further comprising:
a proximally-positioned hub for securing the cannula to the pump.

20. The cannula of claim 1 further comprising:
a distally-positioned tip, wherein the distally-positioned tip is configured to be inserted through a wall of one of the heart, an artery, or a vein of the patient.

21. The cannula of claim 20, wherein the distally-positioned tip has an outer surface and at least a portion of the outer surface includes a porous in-growth material.

22. The cannula of claim 20, wherein the distally-positioned tip includes at least one anchor that extends radially from the distally-positioned tip and is configured to resist a proximally-directed force applied to the cannula.

23. The cannula of claim 22, wherein the distally-positioned tip has an outer surface including a porous in-growth material adjacent to the at least one anchor.

24. The cannula of claim 23, wherein the porous in-growth material on the outer surface further includes a prothrombotic coating.

25. The cannula of claim 22, wherein the distally-positioned tip is secured to the cannula by at least one barb, at least one suture, or at least one band.

26. The cannula of claim 25, wherein the at least one band further includes a porous in-growth material.

27. The cannula of claim 1, wherein at least a part of the distal portion of the liner is configured to create an anastomotic connection with a wall of one of the heart, an artery, or a vein.

28. The cannula of claim 1, wherein the cannula includes a distal end and a proximal end and a tapered inner diameter extending therebetween.

29. The cannula of claim 1, wherein the porous in-growth material from which the liner and the outer layer are constructed is a thermoset material and the jacket is constructed from a thermoplastic material, and the jacket is bonded to the liner and the outer layer with application of heat.

30. A cannula for moving blood between a pump and the circulatory system of a patient, the cannula comprising:
a liner having a length and comprising an intermediate portion that extends for a majority of the length between a proximal portion and a distal portion, and a lumen extending between the proximal and distal portions, wherein at least the intermediate portion is constructed from a porous in-growth material that permits embedment therein of endothelial cells of blood flowing through the lumen to thereby reduce thrombus formations along an inner blood contacting surface of the cannula, the proximal portion is configured for connecting to the pump and the distal portion is configured for connecting to the circulatory system;

a reinforcing structure surrounding at least a part of the intermediate portion of the liner for resisting kinks along the length of the cannula;
a jacket surrounding the reinforcing structure and fully encapsulating the liner; and
a continuous outer layer bonded to and surrounding the jacket and extending along a full length of the intermediate and distal portions of the liner, the outer layer constructed from a porous in-growth material that permits embedment therein of endothelial cells of blood flowing along an outer blood contacting surface of the cannula to thereby reduce thrombus formations along the outer blood contacting surface.

31. The cannula of claim 30, wherein the porous in-growth material is a porous polymeric material, a woven polyester material, or a velour.

32. The cannula of claim 30, wherein the proximal and distal portions of the liner are constructed from a polymer material.

33. The cannula of claim 30, wherein the liner is constructed as a unitary structure having the distal, intermediate, and proximal portions constructed from the porous in-growth material.

34. The cannula of claim 30, wherein the reinforcing structure is constructed from stainless steel, chromium cobalt, a superelastic material, or a rigid polymeric material.

35. The cannula of claim 30, wherein the jacket is constructed from a polymeric material and is bonded to the liner.

36. The cannula of claim 30 further comprising:
a distally-positioned tip, wherein the distally-positioned tip is configured to be inserted through a wall of one of the heart, an artery, or a vein of the patient.

37. The cannula of claim 36, wherein the distally-positioned tip has an outer surface and at least a portion of the outer surface includes a porous in-growth material.

38. The cannula of claim 36, wherein the distally-positioned tip is secured to the cannula by at least one barb, at least one suture, or at least one band.

39. The cannula of claim 30 further comprising:
a proximally-positioned hub for connecting the cannula to the pump.

40. The cannula of claim 30 further comprising:
one or more longitudinal strengtheners positioned between the liner and the jacket, extending, at least partially, between the proximal and distal portions.

41. An inflow cannula for moving blood from the heart of a patient to a pump, the inflow cannula comprising:
a liner having a length and comprising an intermediate portion that extends for a majority of the length between a proximal portion and a distal portion, and a lumen extending between the proximal and distal portions, wherein at least the intermediate portion is constructed from a porous in-growth material that permits embedment therein of endothelial cells of blood flowing through the lumen to thereby reduce thrombus formations along an inner blood contacting surface of the cannula;
a jacket fully encapsulating the liner;
a continuous outer layer bonded to and surrounding the jacket and extending along a full length of the intermediate and distal portions of the liner, the outer layer constructed from a porous in-growth material that permits embedment therein of endothelial cells of blood flowing along an outer blood contacting surface of the cannula to thereby reduce thrombus formations along the outer blood contacting surface;

a tip coupled to the distal portion of the liner and configured to be inserted through a wall of the heart; and a hub coupled to the proximal portion of the liner and configured to secure the inflow cannula to the pump.

42. The inflow cannula of claim 41 further comprising:

a reinforcing structure surrounding at least a part of the intermediate portion of the liner for resisting kinks along the length of the inflow cannula.

43. The inflow cannula of claim 41, wherein the tip includes at least one anchor that extends radially from the tip and is configured to resist a proximally-directed force applied to the inflow cannula.

44. The inflow cannula of claim 43, wherein the tip has an outer surface including a porous in-growth material adjacent to the at least one anchor.

45. The inflow cannula of claim 44 wherein the porous in growth material on the outer surface further includes a prothrombotic coating.

46. The inflow cannula of claim 41, wherein the tip is secured to the inflow cannula by at least one barb, at least one suture, or at least one band.

47. The inflow cannula of claim 41, wherein the inflow cannula extends percutaneously from the heart to the pump.

48. The inflow cannula of claim 41 further comprising:

one or more longitudinal strengtheners positioned between the liner and the jacket, extending, at least partially, between the proximal and distal portions.

49. An outflow cannula for moving blood from a pump to an arterial structure within the vascular network of a patient, the outflow cannula comprising:

a liner having a length and comprising an intermediate portion that extends for a majority of the length between a proximal portion and a distal portion, and a lumen extending between the proximal and distal portions, wherein at least the intermediate portion is constructed from a porous in-growth material that permits embedment therein of endothelial cells of blood flowing through the lumen to thereby reduce thrombus formations along an inner blood contacting surface of the cannula;

a jacket fully encapsulating the liner;

a continuous outer layer bonded to and surrounding the jacket and extending along a full length of the intermediate and distal portions of the liner, the outer layer constructed from a porous in-growth material that permits embedment therein of endothelial cells of blood flowing along an outer blood contacting surface of the cannula to thereby reduce thrombus formations along the outer blood contacting surface;

a hub coupled to the proximal portion of the liner and configured to secure the outflow cannula to the pump; and a distal end that is configured to be coupled to the arterial structure.

50. The outflow cannula of claim 49 further comprising:

a reinforcing structure surrounding at least a part of the intermediate portion of the liner for resisting kinks along the length of the outflow cannula.

51. The outflow cannula of claim 49, wherein the distal portion of the liner is also constructed from the porous in-growth material having an outer diameter that is larger than an outer diameter of the porous in-growth material comprising the intermediate portion of the liner.

52. The outflow cannula of claim 49, wherein the distal end includes an anastomotic connector.

* * * * *